(12) United States Patent
Brunsvold et al.

(10) Patent No.: US 10,881,500 B2
(45) Date of Patent: Jan. 5, 2021

(54) MULTIPLE ANCHOR TENSION ADJUSTMENT SYSTEM AND METHOD

(71) Applicant: Parcus Medical, LLC, Sarasota, FL (US)

(72) Inventors: Mark D. Brunsvold, Sarasota, FL (US); Barton W. Bracy, Orlando, FL (US); Anderson A. Brunsvold, Sarasota, FL (US)

(73) Assignee: PARCUS MEDICAL, LLC, Sarasota, FL (US)

( * ) Notice: Subject to any disclaimer, the term of this patent is extended or adjusted under 35 U.S.C. 154(b) by 0 days.

(21) Appl. No.: 16/283,205

(22) Filed: Feb. 22, 2019

(65) Prior Publication Data

US 2020/0268502 A1 Aug. 27, 2020

(51) Int. Cl.
*A61F 2/08* (2006.01)
*A61B 17/88* (2006.01)
*A61B 17/04* (2006.01)

(52) U.S. Cl.
CPC ........ *A61F 2/0811* (2013.01); *A61B 17/8869* (2013.01); *A61B 2017/0414* (2013.01); *A61B 2017/0464* (2013.01); *A61F 2002/0852* (2013.01)

(58) Field of Classification Search
CPC .......... A61F 2/0811; A61F 2002/0852; A61B 17/0401; A61B 17/8869; A61B 2017/0414; A61B 2017/0464; A61B 17/0482; A61B 2017/00336; A61B 2017/00858; A61B 2017/044; A61B 2017/0417; A61B 2017/0477; A61B 2017/06185; A61B 2017/0882
See application file for complete search history.

(56) References Cited

U.S. PATENT DOCUMENTS

| | | | |
|---|---|---|---|
| 7,585,311 B2 | 9/2009 | Green et al. | |
| 9,717,587 B2 | 8/2017 | Dougherty et al. | |
| 9,782,250 B2 | 10/2017 | Dougherty et al. | |
| 9,999,496 B2 | 6/2018 | Dougherty et al. | |
| 10,149,752 B2 | 12/2018 | Dougherty et al. | |
| 2008/0065114 A1 | 3/2008 | Stone et al. | |
| 2013/0165972 A1* | 6/2013 | Sullivan ............ | A61B 17/0401 606/232 |
| 2014/0277121 A1* | 9/2014 | Pilgeram ............ | A61B 17/0401 606/228 |

(Continued)

FOREIGN PATENT DOCUMENTS

WO 2016141072 9/2016

*Primary Examiner* — Wade Miles
*Assistant Examiner* — Kankindi Rwego
(74) *Attorney, Agent, or Firm* — Fox Rothschild LLP

(57) ABSTRACT

An orthopedic attachment system includes a first bone anchor, a second bone anchor, and a flexible connector. The flexible connector is connected between the first bone anchor and the second bone anchor. The flexible connector includes a sliding loop, a tensioning end and a fixed end. The sliding loop is connected to a sling loop bone anchor, and the fixed end is connected to the fixed end bone anchor. The tensioning end is slidably connected and lockable to the fixed end. A flexible connector, a method for attaching a flexible connector between at least two bone anchors in a patient's body, and a method of making a flexible connector are also disclosed.

10 Claims, 19 Drawing Sheets

(56) References Cited

U.S. PATENT DOCUMENTS

2017/0319327 A1    11/2017  Dougherty et al.
2018/0221010 A1*   8/2018   Lund .................. A61B 17/0401
2019/0053888 A1    2/2019   Dougherty et al.

* cited by examiner

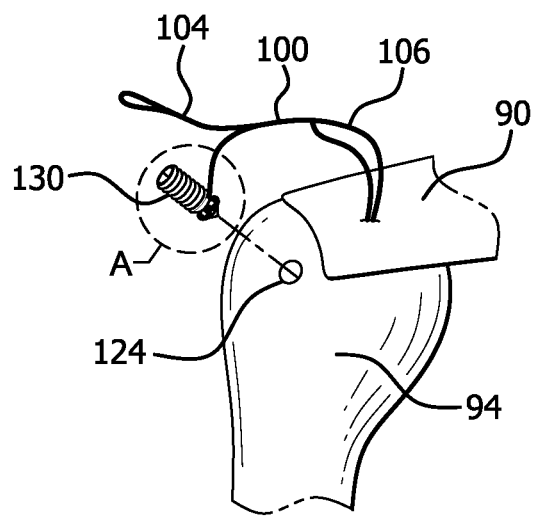
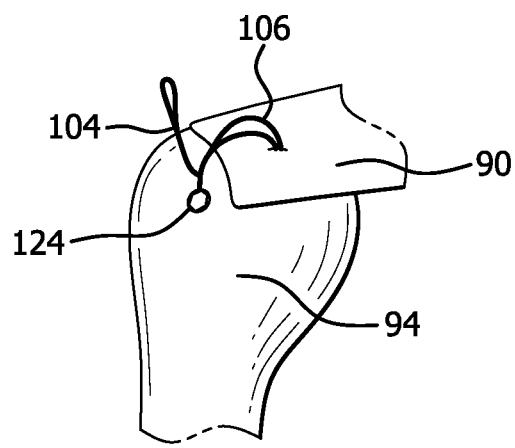
FIG. 9　　　　　　FIG. 10
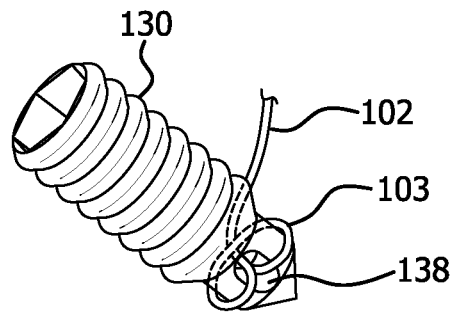
FIG. 9A
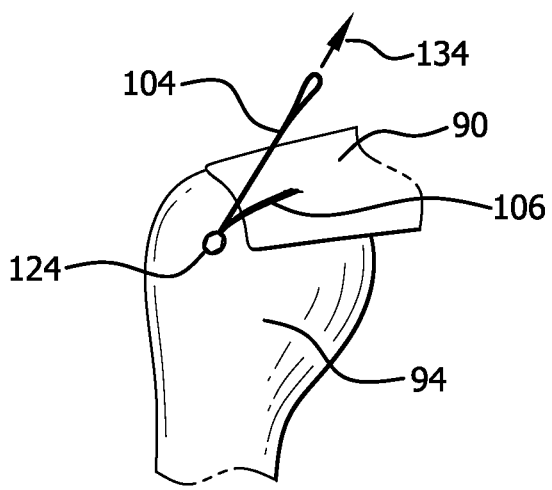
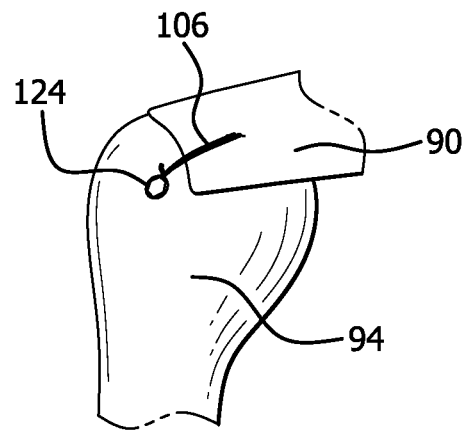
FIG. 11　　　　　　FIG. 12

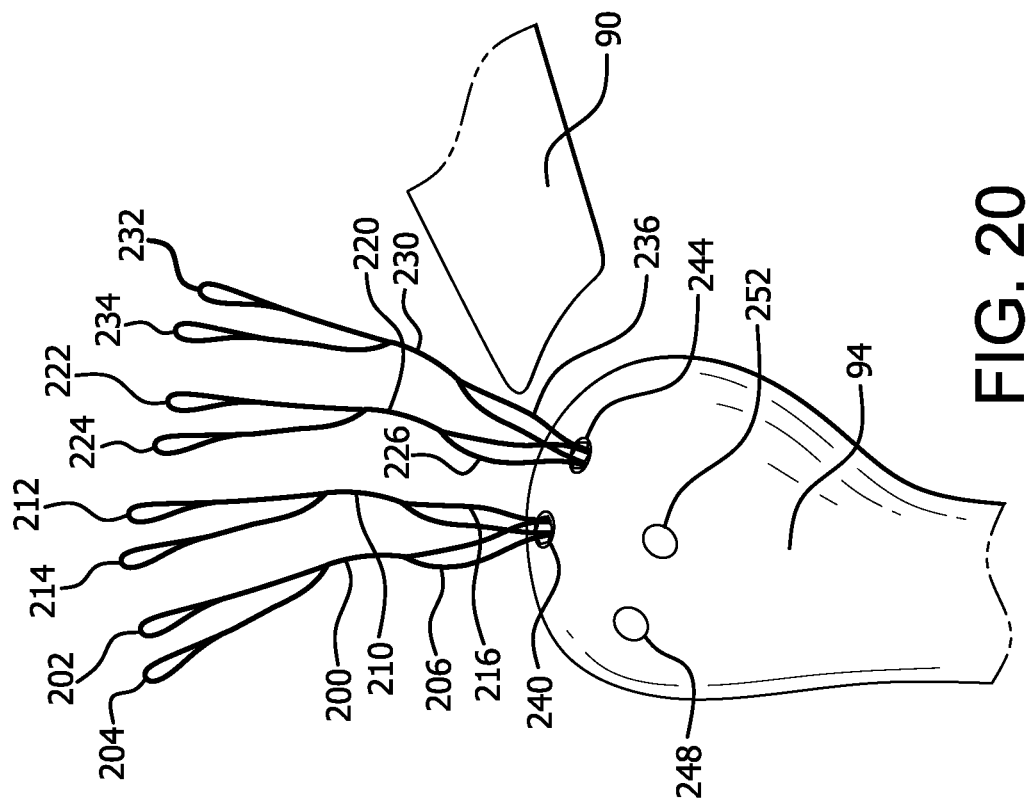
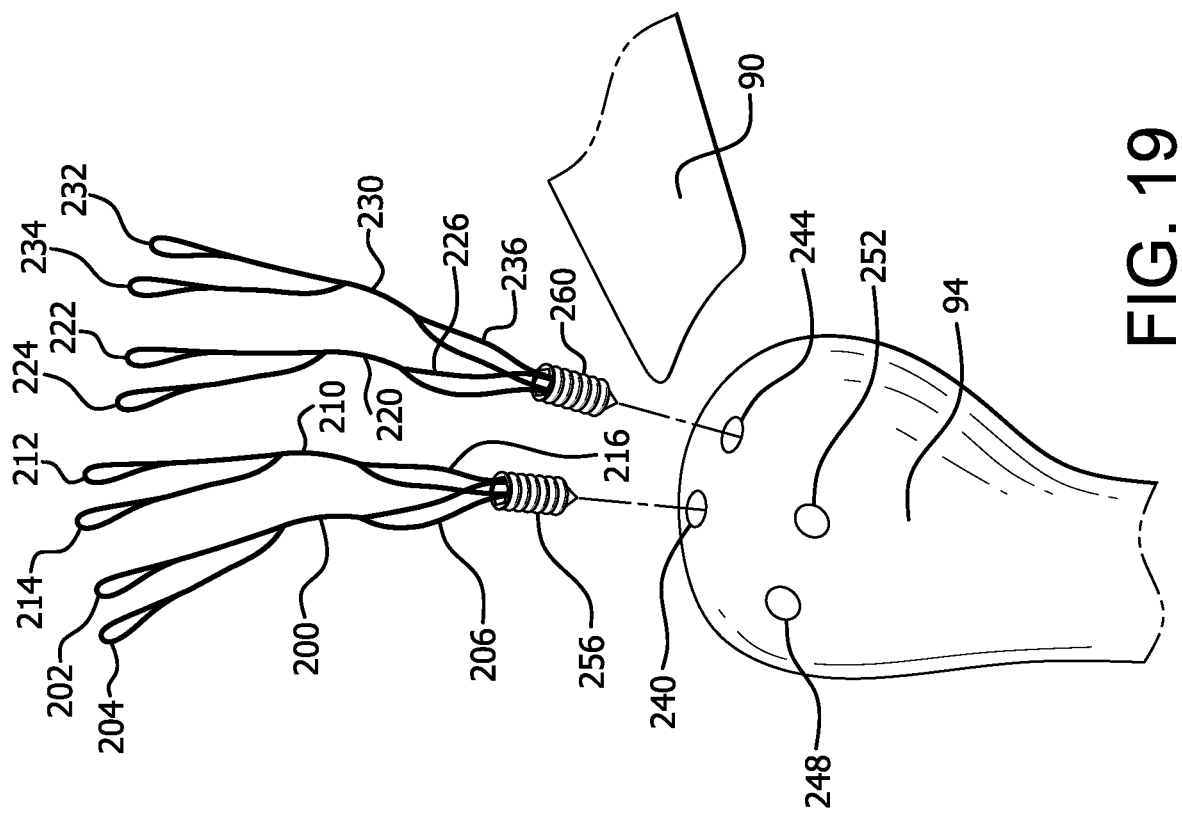

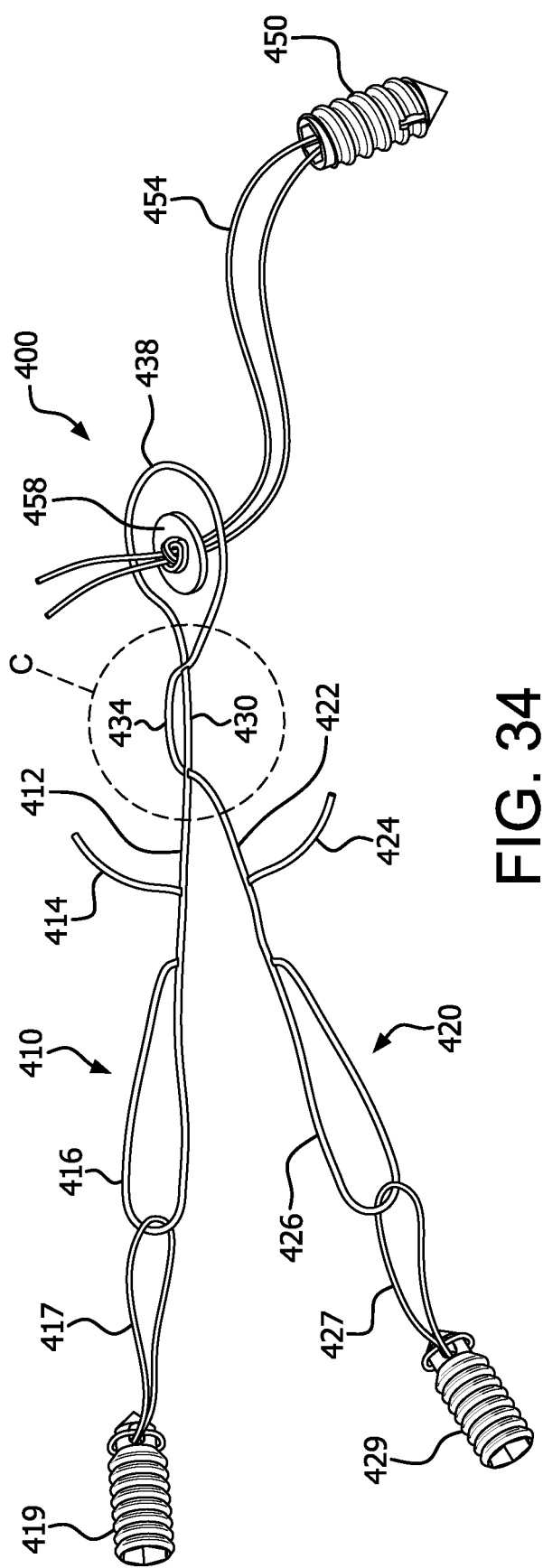
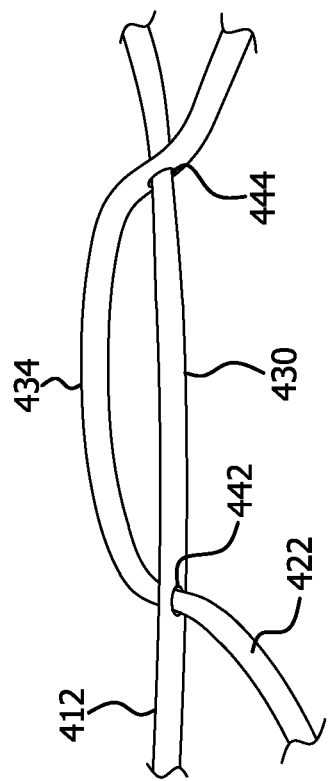
FIG. 34
FIG. 35

MULTIPLE ANCHOR TENSION ADJUSTMENT SYSTEM AND METHOD

FIELD OF THE INVENTION

The present invention relates to adjustable fixation devices and more particularly to adjustable graft fixation devices for surgical applications.

BACKGROUND OF THE INVENTION

The ability to fix tissue effectively is central to the surgical process. In surgery, and in particular in arthroscopic surgery, fixation of tissue must be achieved under constraints of limited access. It is understood by those of skill in the art that fixation failure is a particularly important failure mode in the early postoperative period, and although many fixation approaches have been developed, the need for continued improvement remains widely acknowledged.

While a variety of techniques have been developed for coupling grafts of soft tissue to bone, it remains difficult to achieve good results in certain particularly demanding procedures. Where multiple fixation devices are necessary, applying the desired tension to the graft is particularly challenging and typically requires some amount of approximation in the selection and sizing of the surgical devices to result in the desired tension.

SUMMARY OF THE INVENTION

An orthopedic attachment system includes a flexible connector comprising a sliding loop at a proximal end, a fixed end at a distal end, and a tensioning end. A sliding loop bone anchor can be connected to the sliding loop. A fixed end anchor can be connected to the fixed end. The tensioning end can be slidably connected and lockable to the fixed end.

The sliding loop can be formed by a first sliding axial connection of the tensioning end through the fixed end. The tensioning end enters at a proximal entering location on the fixed end and exits at a distal exiting location on the fixed end.

The flexible connector can further include a distal transverse sliding connection with the tensioning end passing transversely through the fixed end at a distal location on the fixed end relative to the first sliding axial connection. The flexible connector can include a locking sliding connection formed by threading the tensioning end through the fixed end at a position proximal to the distal transverse sliding connection.

The locking sliding connection can include a proximal transverse sliding connection with the tensioning end passing transversely through the fixed end at a location between the distal transverse sliding connection and the distal exiting location of the first sliding axial connection. The fixed end of the flexible connector can have lateral sides, and the distal transverse sliding connection has an entry and an exit on the fixed end, and the proximal transverse sliding connection has an entry and an exit on the fixed end. The distal exiting location of the sliding axial connection, the entry of the distal transverse sliding connection, and the exit of the proximal transverse sliding connection can be on the same lateral side of the fixed end of the flexible connector.

The sliding locking connection can include a second axial sliding connection adjacent to the first axial sliding connection. Upon tensioning of the tensioning end, the tensioning end slides distally at the first axial sliding connection and slides proximally at the second axial sliding connection. The second axial sliding axial connection can be formed with the tensioning end entering at the exiting location of the first axial sliding connection, and exiting at the entering location of the first axial sliding connection.

The orthopedic attachment system can include first and second flexible connectors and first and second sliding loop anchors. The sliding loop ends of the first and second flexible connectors can be connected to the first and second sliding loop anchors. The fixed ends of the first and second flexible connectors can be attached to a fixed end anchor.

The orthopedic adjustment system can include first and second flexible connectors attached at sliding loop ends to a first sliding loop anchor, third and fourth flexible connectors attached at sliding loop ends to a second sliding loop anchor, and first and second fixed end anchors. The fixed ends of the first and third flexible connectors can be secured to the first fixed end anchor. The fixed ends of the second and fourth flexible connectors can be secured to the second fixed end anchor.

The fixed end and tensioning end of the flexible connector can include loops. The fixed end anchor can be at least one selected from the group consisting of a knotless anchor, an all suture anchor, and a sleeved suture anchor. The flexible connector is braided, and sliding connections can be formed by threading the tensioning end of the braided flexible connector through the fixed end. The flexible connector can be double sided with a sliding loop at each end. The sliding loops can be connected by a common fixed end.

A method for attaching a flexible connector between at least two bone anchors in a patient's body can include the step of providing a flexible surgical connector, comprising a sliding loop, a fixed end and a tensioning end, the tensioning end being slidably connected and lockable to the fixed end. A sliding loop bone anchor is provided, and is connectable to the sliding loop bone anchor. A fixed end bone anchor is provided, and is connectable to the fixed end bone anchor. The sliding loop of the flexible connector is connected to the sliding loop bone anchor to form a flexible connector assembly. The flexible connector assembly is installed at a patient target location. The fixed end of the flexible connector is attached to the fixed end bone anchor. The fixed end bone anchor and the fixed end of the flexible connector are installed at a second patient target location. Tension is applied to the tensioning end to tension the flexible connector between the sliding loop bone anchor and the fixed end bone anchor, and to lock the tensioning end to the fixed end.

The flexible connector and the sliding loop bone anchor can be provided as a pre-connected flexible connector assembly. The flexible connector, the sliding loop bone anchor, and the fixed end bone anchor can be provided as a pre-connected flexible connector assembly. A graft can be secured to and between the sliding loop and the sliding loop bone anchor, and the fixed end and the fixed end bone anchor.

A flexible surgical connector can include a sliding loop, a fixed end and a tensioning end. The sliding loop can be connectable to a first bone anchor. The fixed end can be connectable to a second bone anchor. The tensioning end can be slidably connected to and lockable to the fixed end.

A method of making a flexible connector for surgical applications can include the step of providing a flexible connector having a fixed end and a tensioning end. A first axial sliding connection can be formed by axially threading the tensioning end through the fixed end to form a sliding loop. The axial connection can have an entry and an exit location. The fixed end can be distal to the sliding loop. A first transverse sliding connection can be formed by transversely threading the tensioning end through the fixed end at a location distal to the exiting location of the axial connection. A locking sliding connection can be formed by threading the tensioning end through the fixed end proximal to the first transverse sliding connection.

The locking sliding connection can include a second transverse sliding connection formed by transversely threading the tensioning end through the fixed end at a location between the exiting location of the first axial sliding connection and the first transverse sliding connection. The locking sliding connection can include a second axial sliding connection that is adjacent to the first axial sliding connection, and wherein upon tensioning of the tensioning end, the tensioning end slides distally at the first axial sliding connection and slides proximally at the second axial sliding connection.

BRIEF DESCRIPTION OF THE DRAWINGS

There are shown in the drawings embodiments that are presently preferred it being understood that the invention is not limited to the arrangements and instrumentalities shown, wherein:

FIG. 9 is a schematic drawing of the orthopedic attachment system in a fifth stage of the orthopedic attachment procedure.

FIG. 9A is a perspective view, partially in phantom of area A in FIG. 9.

FIG. 10 is a schematic drawing of the orthopedic attachment system in a sixth stage of the orthopedic attachment procedure.

FIG. 11 is a schematic drawing of the orthopedic attachment system in a seventh stage of the orthopedic attachment procedure.

FIG. 12 is a schematic drawing of the orthopedic attachment system in an eighth stage of the orthopedic attachment procedure.

FIG. 19 is a schematic drawing of a double-row orthopedic attachment system in a first stage of an orthopedic attachment procedure.

FIG. 20 is a schematic drawing of the orthopedic attachment system of FIG. 19, in a second stage of the orthopedic attachment procedure.

FIG. 34 is a perspective view of a double-sided flexible connector embodiment.

FIG. 35 is an expanded view of area C in FIG. 34.

DETAILED DESCRIPTION OF THE INVENTION

Figure 1:
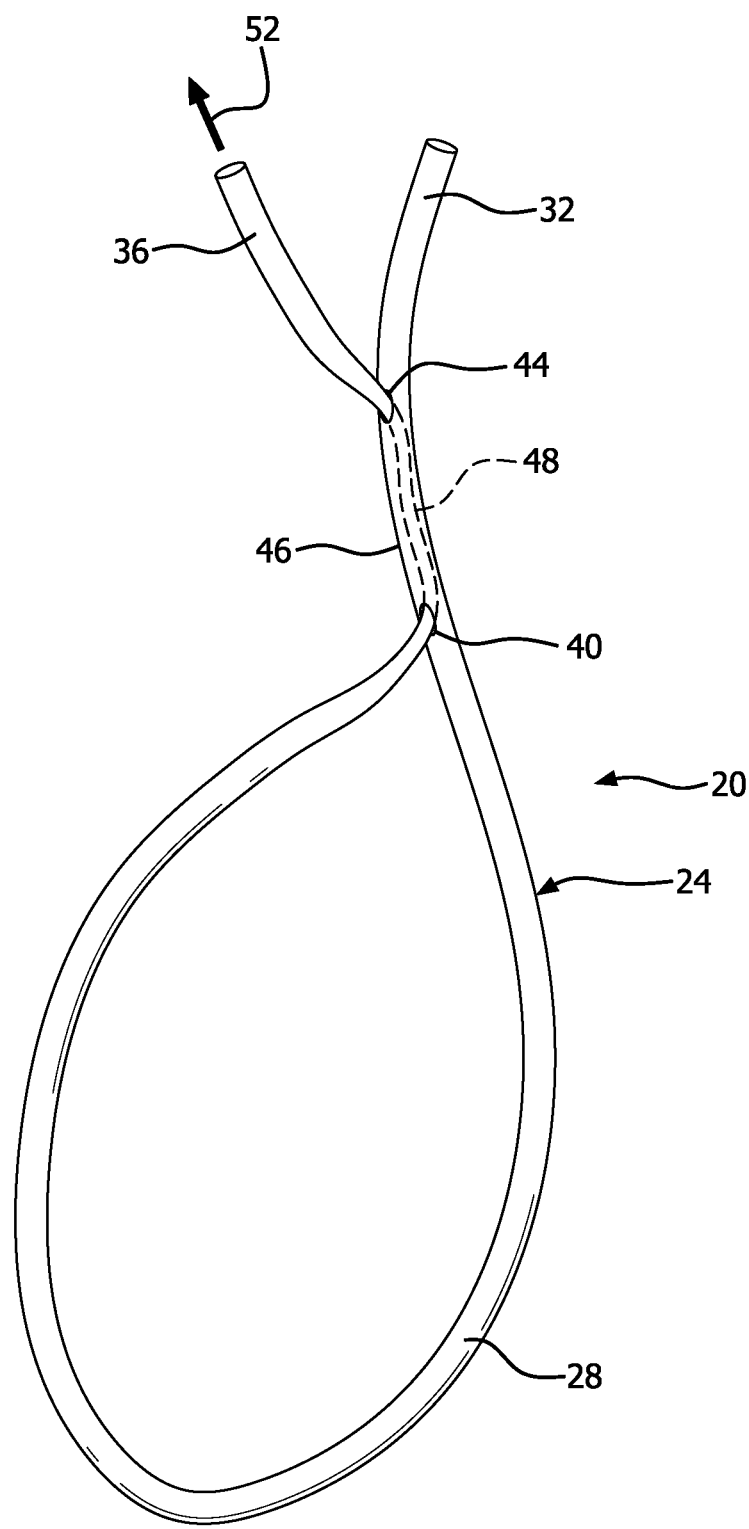
FIG. 1 is a plan view, partially in phantom, of a flexible connector in a first stage of assembly.

An orthopedic attachment system includes a flexible connector comprising a sliding loop, a fixed end, and a tensioning end. The sliding loop is connected to a sliding loop bone anchor. The connection can be slidable. The fixed end is connected to a fixed end anchor. The tensioning end is slidably connected and then lockable to the fixed end.

The flexible connector can be made of any flexible, durable surgical grade material. The flexible connector can be made from polymeric or metallic surgical grade materials. The flexible connector can be braided or monofilament.

Sliding connections can be formed by threading the braided flexible connector through itself. Other flexible connector materials are possible.

The flexible surgical connector and the sliding loop bone anchor can be provided as a pre-connected flexible connector assembly. The flexible surgical connector, the sliding loop bone anchor, and the fixed end bone anchor can be provided as a pre-connected flexible connector assembly.

A flexible surgical connector can include a sliding loop, a fixed end and a tensioning end. The sliding loop can be connected to a first bone anchor. The fixed end can be connectable to a second bone anchor, the tensioning end being slidably connected and lockable to the fixed end. The connection between the sliding loop and the sliding loop bone anchor can be capable of sliding.

A method of making a flexible connector for surgical applications can include the step of providing a flexible connector having a fixed end and a tensioning end. A first axial sliding connection can be formed by axially threading the tensioning end through the fixed end to form a sliding loop. The axial connection can have an entry and an exit location. The fixed end can be distal to the sliding loop. A first transverse sliding connection can be formed by transversely threading the tensioning end through the fixed end at a location distal to the exiting location of the axial connection. A locking sliding connection can be formed by threading the tensioning end through the fixed end proximal to the first transverse sliding connection.

The locking sliding connection can include a second transverse sliding connection formed by transversely threading the tensioning end through the fixed end at a location between the exiting location of the first axial sliding connection and the first transverse sliding connection. The locking sliding connection can include a second axial sliding connection that is adjacent to the first axial sliding connection, and wherein upon tensioning of the tensioning end, the tensioning end slides distally at the first axial sliding connection and slides proximally at the second axial sliding connection.

The sliding loop can be formed by a sliding axial connection of the tensioning end through the fixed end. The tensioning end enters at a proximal entering location on the fixed end and exits at a distal exiting location on the fixed end. The sliding axial connection can also be accomplished with a suitable connector.

The flexible connector can further include a distal transverse sliding connection with the tensioning end passing transversely through the fixed end at a distal location on the fixed end. The flexible connector can also include a proximal transverse sliding connection with the tensioning end passing transversely through the fixed end at a location between the distal location and the proximal exiting location of the sliding axial connection.

The flexible connector can have two lateral sides. The distal transverse sliding connection can have an entry and an exit on the fixed end. The proximal transverse sliding connection can have an entry and an exit on the fixed end. The proximal exiting location of the sliding axial connection, the entry of the distal transverse sliding connection, and the exit of the proximal transverse sliding connection can be on the same lateral side of the flexible connector. The proximal exiting location of the sliding axial connection, the entry of the distal transverse sliding connection, and the exit of the proximal transverse sliding connection can be axially aligned on the flexible connector.

FIG. 1 is a plan view of a flexible connector in a first stage of assembly. The flexible connector 20 includes a piece of surgical grade flexible material 24 forming a proximal sliding loop 28, distal fixed end portion 32 and a tensioning end portion 36. The sliding loop 28 is formed by an axial sliding connection between the tensioning end portion 36 and the fixed end portion 32. The axial sliding connection retains portions of the fixed end 32 and tensioning end 36 in coaxial or side-bi-side relationship where the tensioning end 36 can axially slide relative to the fixed end 32 to adjust the dimensions of the sliding loop 28. A double-barreled connector can be secured to the fixed end portion 32 to permit this connection, where the connector would be secured to the fixed end 32 and slidably engage the tensioning and 36 to permit adjustment of the dimensions of the sliding loop 28. In the embodiment shown, tensioning end 36 is axially connected to a portion 46 of fixed end 32 by a coaxial threading of the portion 48 of the tensioning end 36 through a portion 46 of fixed end 32. The tensioning end 36 enters at a proximal entering location 40 and exits at a distal exiting location 44. Adjustment of the dimensions of the sliding loop 24 can be accomplished by applying tension to the tensioning end 36 to move the tensioning end 36 through the portion 46 of the fixed end 32, as shown by arrow 52.

Figure 2:
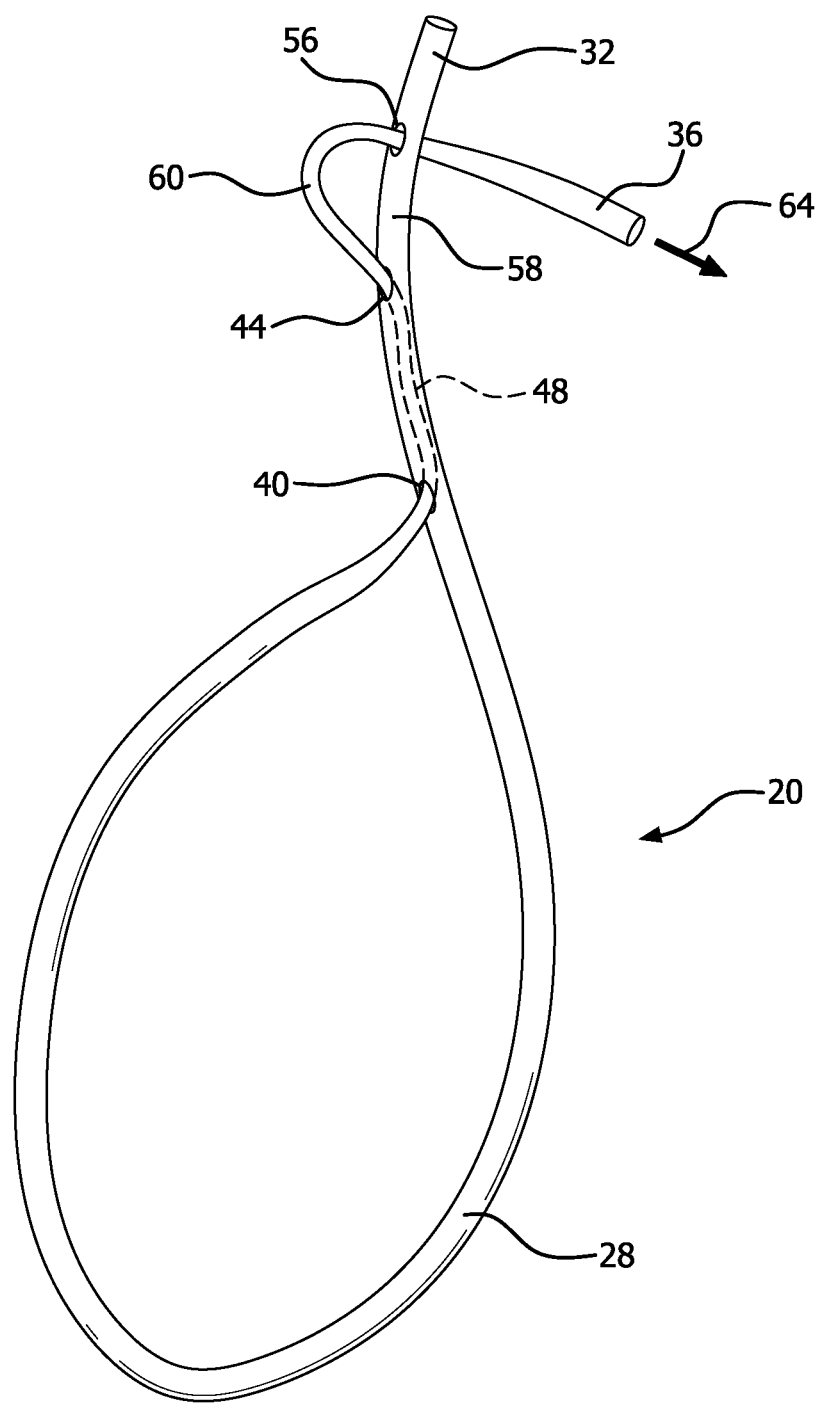
FIG. 2 is a plan view, partially in phantom, of the flexible connector in a second stage of assembly.

FIG. 2 is a plan view of the flexible connector in a second stage of assembly. The tensioning end 36 forms a transverse sliding connection with a portion of the fixed end distal to the exiting location 44. The transverse sliding connection can alternatively be made by a connected fitting of some kind, for example in the form of a cross with one portion engaging the fixed end 32 and the other portion slidably receiving the tensioning end 36 in a perpendicular direction. In the embodiment shown, the tensioning end 36 is threaded through the fixed end 32 at a location 56 forming a locking loop 60 the dimensions of which can be adjusted by tension on the tensioning end 36 as indicated by arrow 64. The exiting location 44 and transverse sliding connection location 56 define a locking portion 58 of the fixed end 32.

Figure 3:
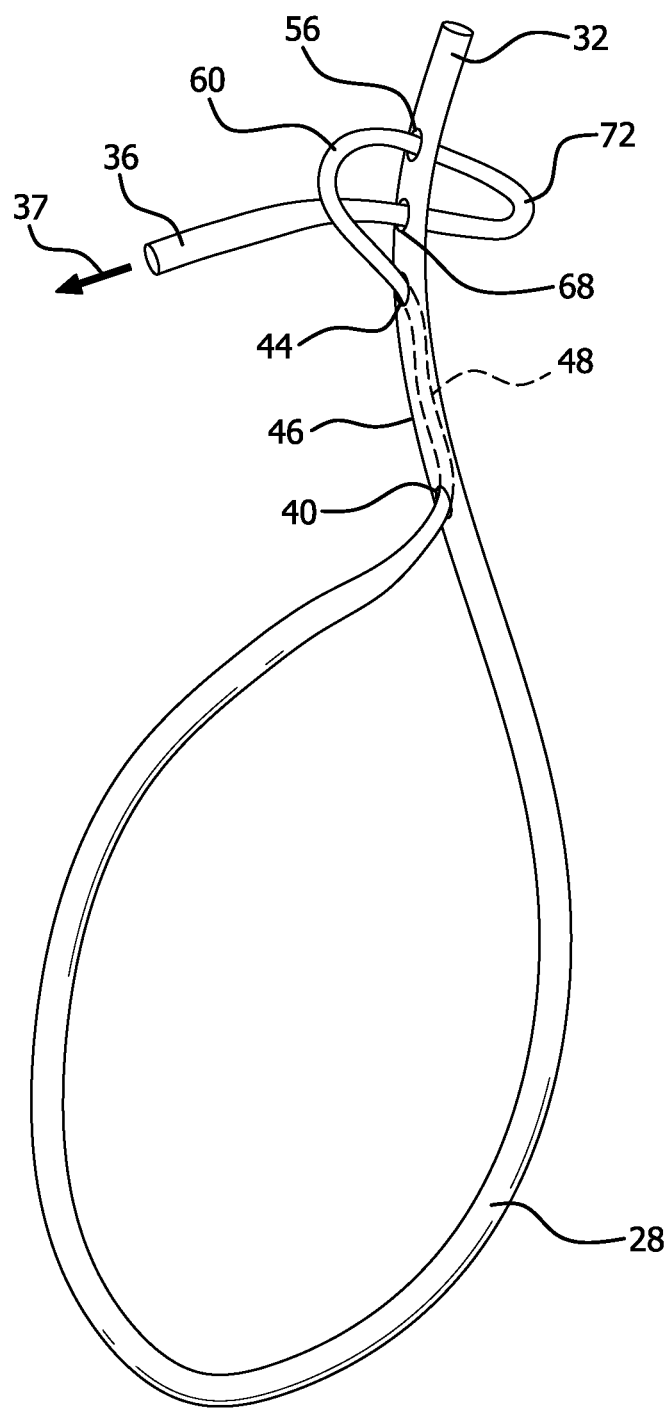
FIG. 3 is a plan view, partially in phantom, of the flexible connector in a third stage of assembly.
Figure 4:
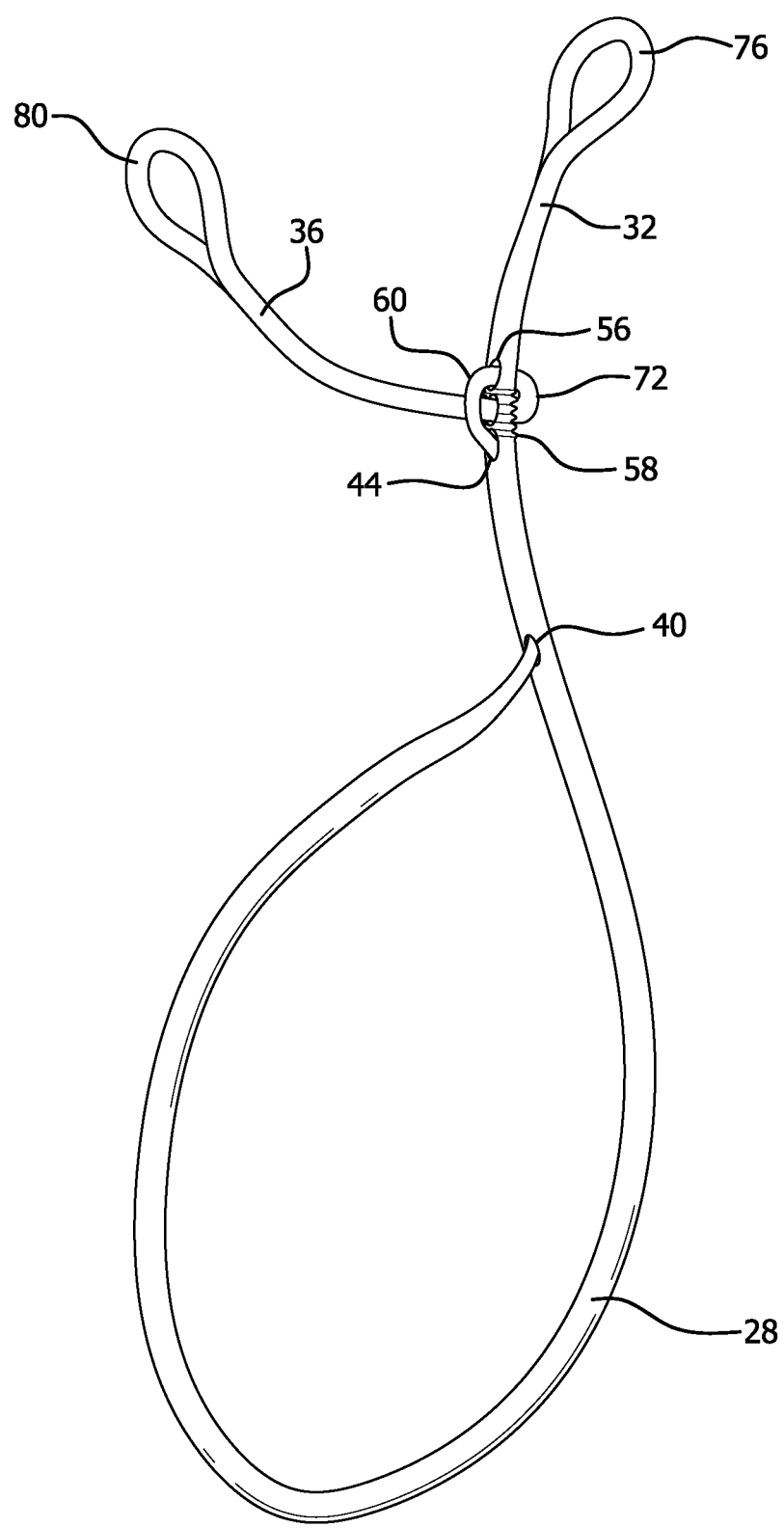
FIG. 4 is a plan view of the flexible connector in a fourth stage of assembly.
Figure 5:
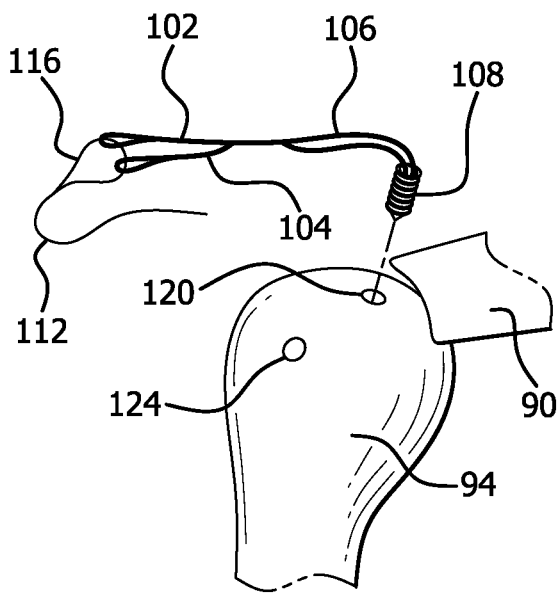
FIG. 5 is a schematic drawing of an orthopedic attachment system according to the invention in a first stage of an orthopedic attachment procedure.

FIG. 3 is a plan view of the flexible connector in a third stage of assembly. The tensioning end 36 forms a locking proximal transverse sliding connection with the fixed end 32 at a location 68 that is between the distal exiting location 44 and the distal transverse sliding location 56 in the locking portion 58. A lock adjustment loop 72 is formed. In the embodiment shown, the distal exiting location 44, the distal transverse sliding location 56, and the proximal transverse sliding location 68 are axially aligned on the fixed end 32. Tension on the tensioning end 36 as indicated by arrow 37 will close the locking loop 60 and the lock adjustment loop 72, and compress the locking portion 58 to secure the tensioning end 36 to the fixed end 32, as shown in FIG. 4. The tensioning end 36 will be secured to the fixed end 32 to fix the dimensions of the sliding loop 28 without additional knots or securing structure on the tensioning end 36. The fixed end 32 can be provided with end loop 76 and the tensioning end 36 can be provided with end loop 80 to facilitate handling and manipulation, if desired.

A method for attaching a flexible connector between at least two bone anchors in a patient's body for a procedure such as to attach graft 90 to a bone such as humerus 94, is shown in FIGS. 5-12. A flexible connector 100 is provided and has a proximal sliding loop 106, fixed end 102 and tensioning end 104. The sliding loop portion 106 is connected to a sliding loop bone anchor 108, the design of which can vary. A suture passer 112 having a loop end 116 to engage end loops of fixed end 102 and tensioning end 104 can be provided to facilitate arthroscopic procedures.

A proximal or medial pilot hole 120 is formed and a distal or lateral pilot hole 124 is also formed during the procedure.

Figure 6:
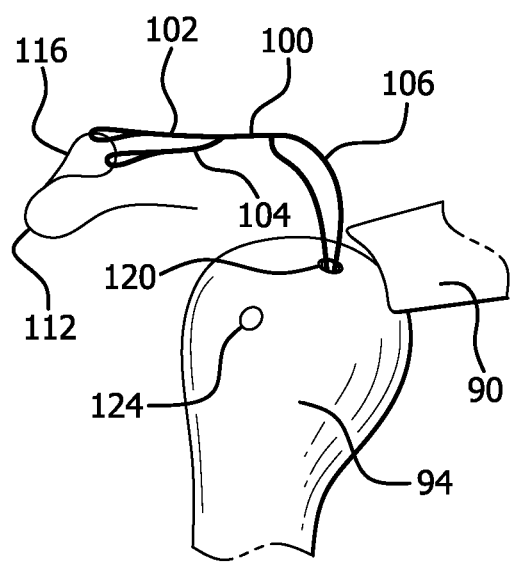
FIG. 6 is a schematic drawing of the orthopedic attachment system in a second stage of the orthopedic attachment procedure.
Figure 7:
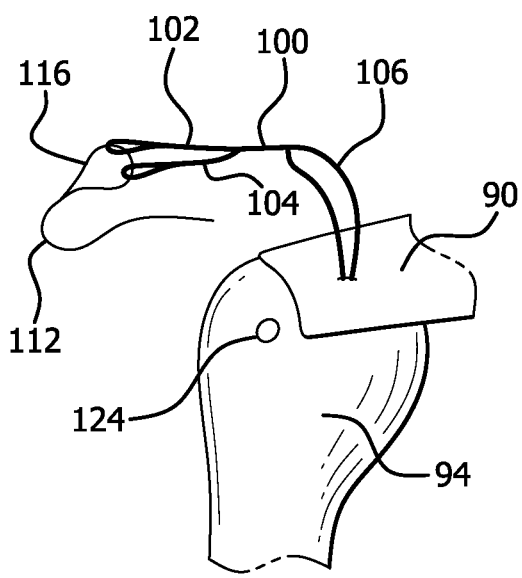
FIG. 7 is a schematic drawing of the orthopedic attachment system in a third stage of the orthopedic attachment procedure.

The proximal pilot hole 120 and lateral pilot hole 124 may be formed at any appropriate part of the procedure. The sliding loop bone anchor 108 is secured in the proximal pilot hole 120 with the sliding loop 106 of the flexible connector 100 attached, as shown in FIG. 6. The flexible connector is then passed through graft 90 and graft 90 is placed in the target location, as shown in FIG. 7.

Figure 8:
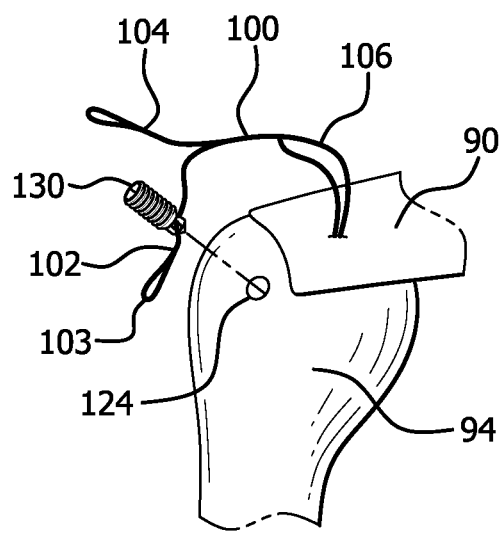
FIG. 8 is a schematic drawing of the orthopedic attachment system in a fourth stage of the orthopedic attachment procedure.

A fixed end bone anchor 130 is threaded onto the fixed end 102 as shown in FIG. 8, and then the fixed end 102 is secured to the bone anchor 130 and positioned over the lateral pilot hole 124 as shown in FIG. 9. The fixed end bone anchor 130 can be of any suitable design. As shown in FIG. 9A the fixed end bone anchor 130 can be a knotless anchor in which the fixed end 102 is looped at portion 103 through aperture 138 in knotless screw 130. Other suture anchors can be utilized.

Tension as indicated by arrow 134 can then be applied to tensioning end 104, as shown in FIG. 11. This will draw the fixed end 102 and reduce the dimensions of the sliding loop 106 until the desired tension is applied to the graft 90. The tension will also cause the locking loop and lock adjustment loop to close and lock the flexible connector 100 and the graft 90 in the desired position. The tensioning end 104 can then be trimmed off as shown in FIG. 12.

A graft is shown secured to and between the sliding loop and the sliding loop anchor, and the fixed end and the fixed end anchor. The invention can be used for procedure in addition to graft fixation procedures, for example to secure implants within the body and additionally to secure different body parts together. The invention is suitable for a variety of minimally invasive procedures, and also for procedures that are not minimally invasive.

Figure 13:
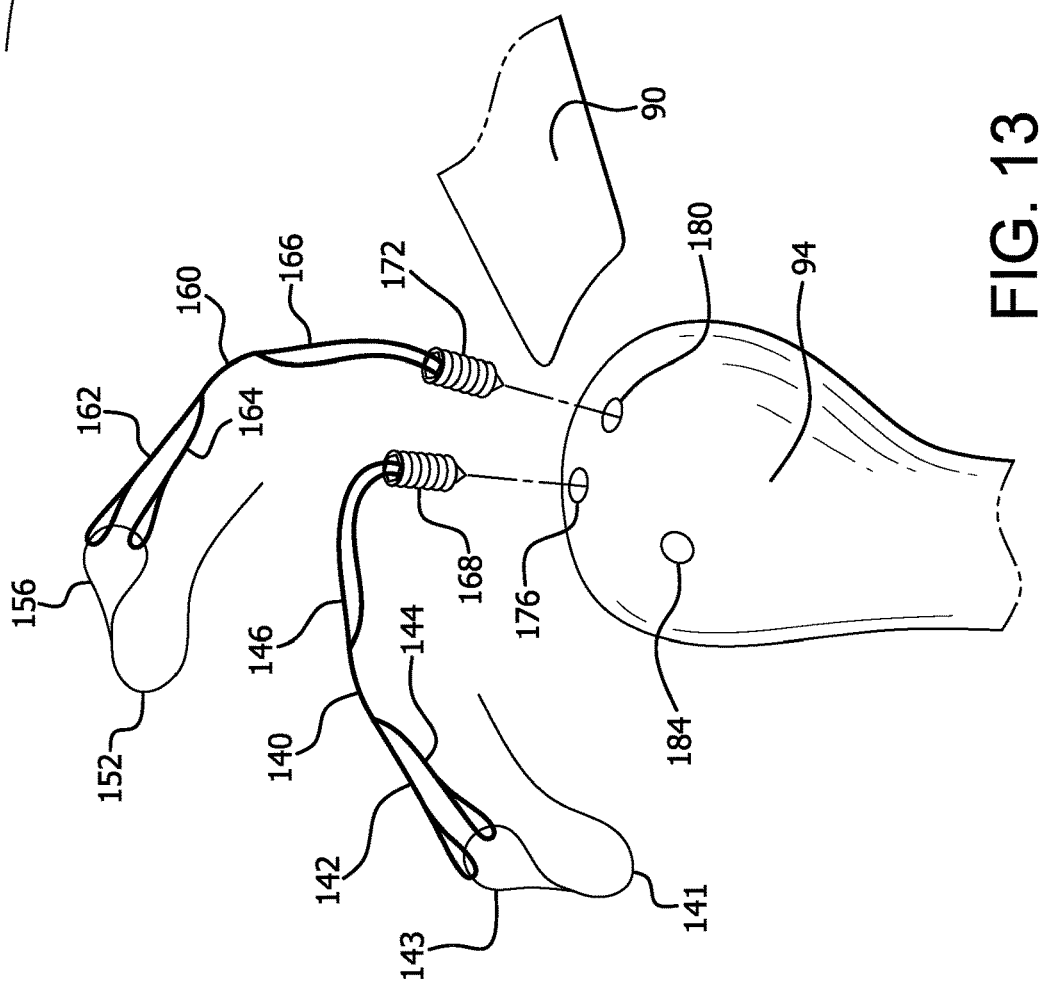
FIG. 13 is a schematic drawing of a two sliding loop anchor, one fixed end anchor orthopedic attachment system in a first stage of the orthopedic attachment procedure.
Figure 16:
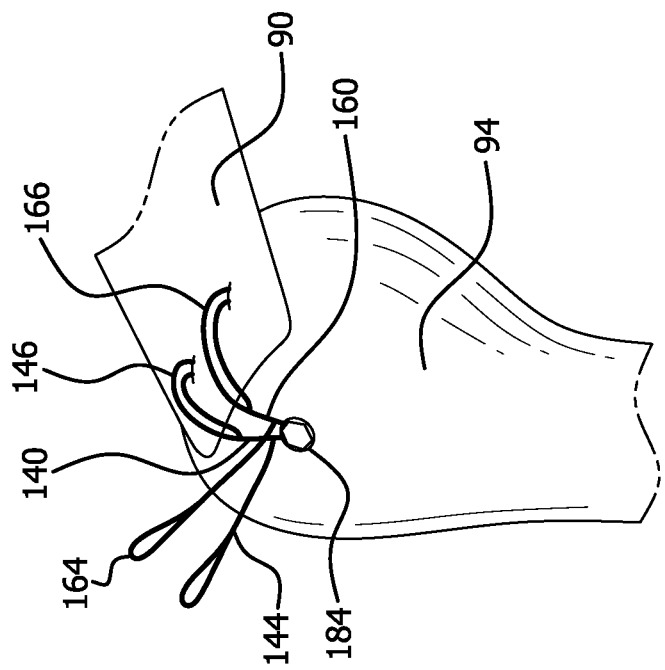
FIG. 16 is a schematic drawing of the orthopedic attachment system of FIG. 13 in a fourth stage of the orthopedic attachment procedure.

The invention is adaptable to procedures where multiple anchors must be placed. FIGS. 13-18 illustrate an embodiment where the procedure calls for two sliding loop anchors, and one fixed end anchor. The embodiment shown is a graft fixation procedure of the graft 90 to the humerus 94. This procedure can begin as shown in FIG. 13 with the placement of a first flexible connector 140. The first flexible connector 140 has a sliding loop 146, a fixed end 142 and a tensioning end 144. The first flexible connector can be secured to a suture passer 141 having an end loop 143. A second flexible connector 160 has a sliding loop 166, a fixed end 162 and a tensioning end 164. The flexible connector 160 can be attached to a suture passer 152 at an end loop 156. The flexible connector 140 is connected to a first sliding loop bone anchor 168. The flexible connector 160 is connected to a second sliding loop bone anchor 172. The first sliding loop bone anchor is placed into a first proximal or medial pilot hole 176 formed in humerus 94. The second sliding loop bone anchor 172 is placed into a second proximal or medial pilot hole 180.

Figure 14:
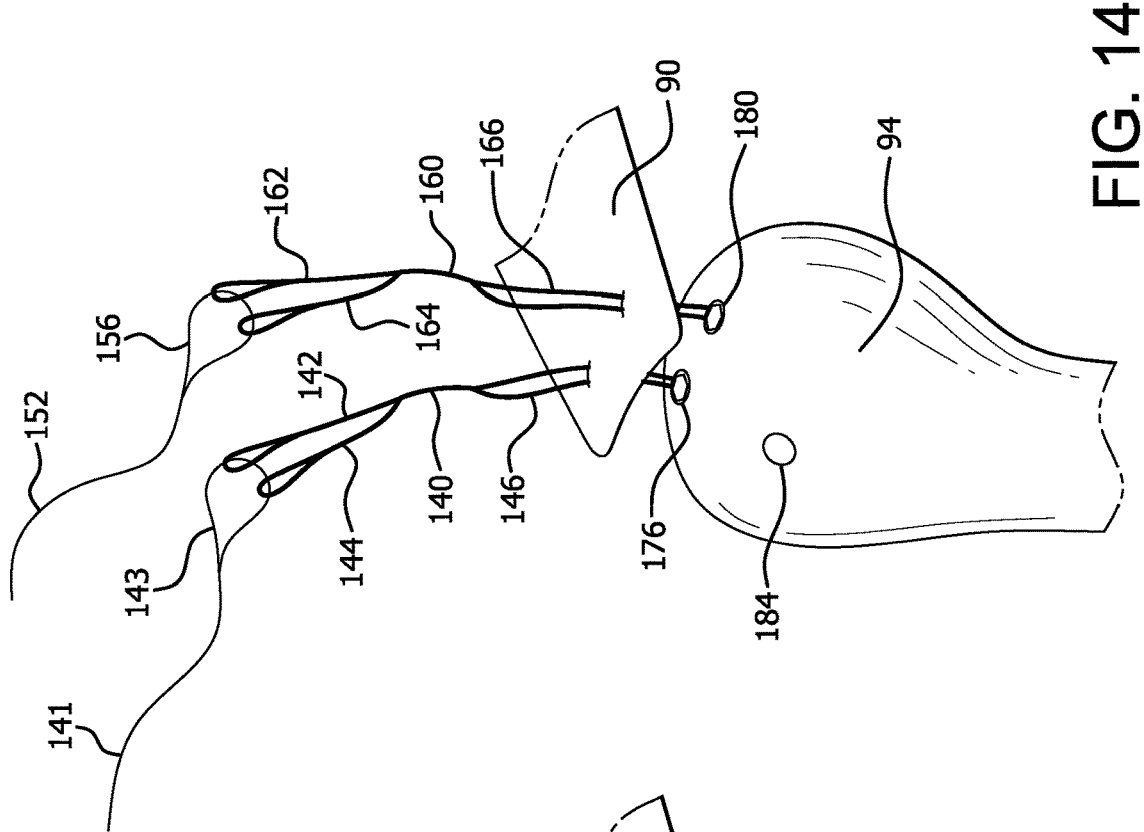
FIG. 14 is a schematic drawing of the orthopedic attachment system of FIG. 13, in a second stage of the orthopedic attachment procedure.
Figure 15:
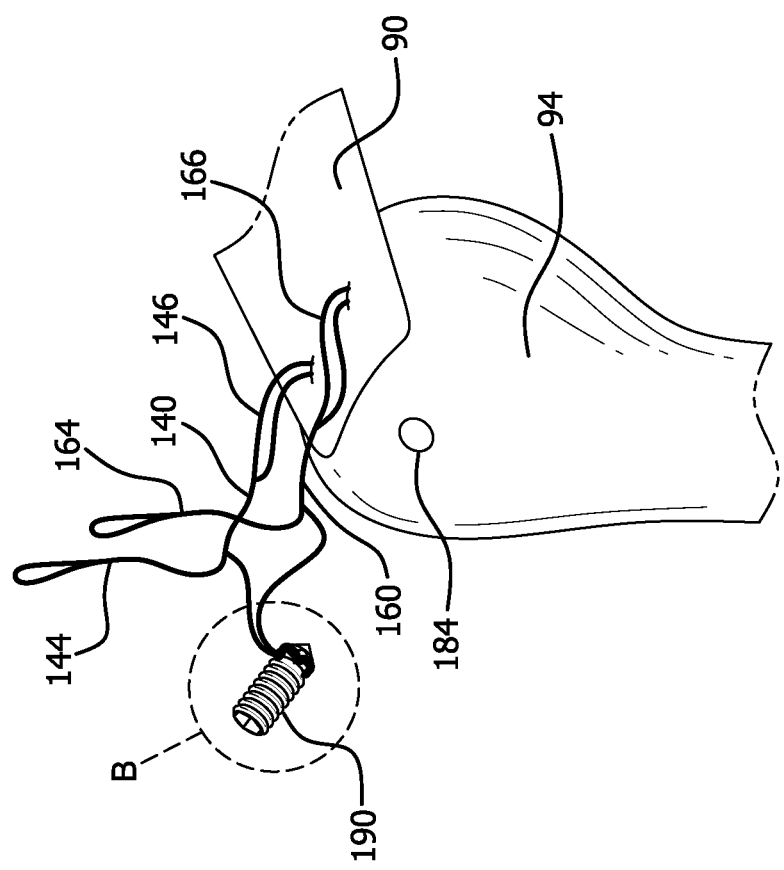
FIG. 15 is a schematic drawing of the orthopedic attachment system of FIG. 13 in a third stage of the orthopedic attachment procedure.
Figure 15A:
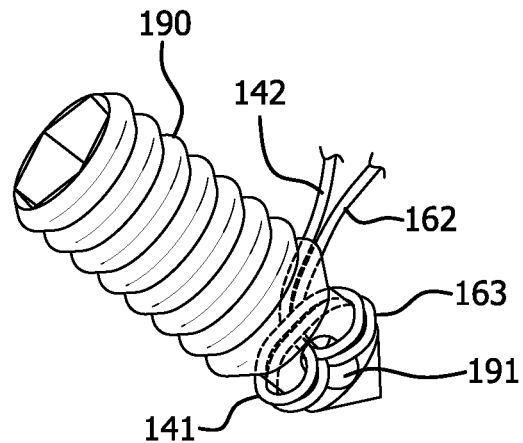
FIG. 15A is a perspective view of area B in FIG. 15.

The first flexible connector 140 and the second flexible connector 160 are then passed through the graft 90, as shown in FIG. 14. The graft 90 is put into position. A distal or lateral pilot hole 184 is formed. As shown in FIG. 15, a fixed end bone anchor 190 is attached to the fixed end 142 of the flexible connector 140 and to the fixed end 162 of the flexible connector 160. As shown in FIG. 15A, the fixed end 142 has a portion 141 threaded through hole 191 of fixed end bone anchor 190 and looped about the bone anchor 190, and the fixed end 162 has a portion 163 threaded through the hole 191 and wrapped about the bone anchor 190 to secure the fixed ends to the fixed end bone anchor 190.

Figure 17:
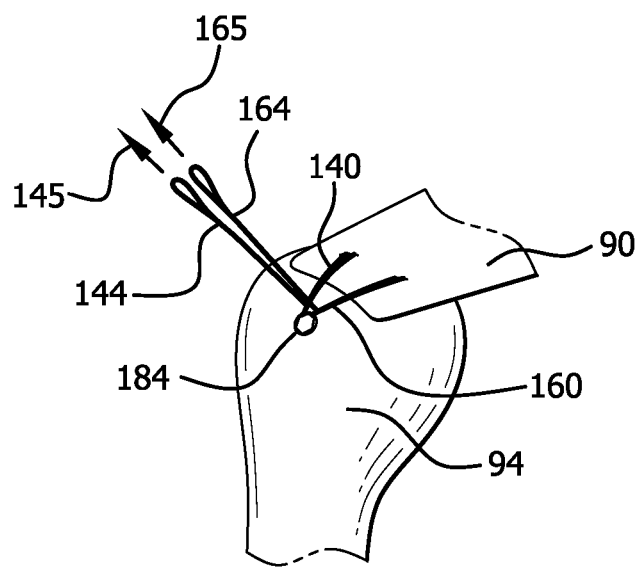
FIG. 17 is a schematic drawing of the orthopedic attachment system of FIG. 13 in a fifth stage of the orthopedic attachment procedure.
Figure 18:
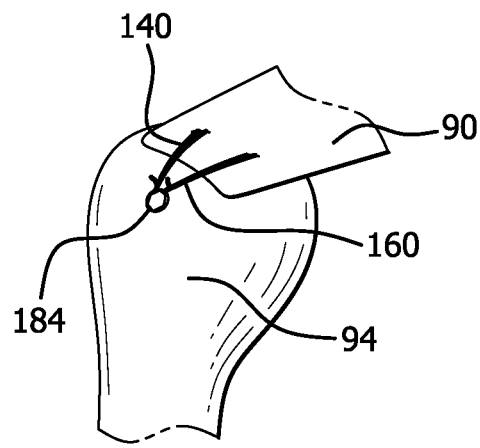
FIG. 18 is a schematic drawing of the orthopedic attachment system of FIG. 13 in a sixth stage of the orthopedic attachment procedure.

The tensioning end 144 can be pulled to apply tension as shown by arrow 145, and the tensioning end 164 can be pulled as shown by arrow 165. This will draw and tighten the sliding loops of the first flexible connector 140 and the second flexible connector 160, as shown in FIG. 17. This will also lock the tensioning end 144 and 164 to the fixed ends 142 and 162. The tensioning end's 144 and 164 can then be trimmed, as shown in FIG. 18.

Some procedures call for a double-row, in which two or more anchors are placed proximally and two or more anchors are placed distally. The invention permits such connections. There is shown in FIGS. 19-27 a double-row procedure with flexible connectors according to the invention where the graft 90 is to be attached to the humerus 94 in a double-row procedure. There is shown in FIG. 19 a first flexible connector 200, a second flexible connector 210, a third flexible connector 220, and a fourth flexible connector 230. The first flexible connector 200 has a sliding loop 206, a fixed end 202 and a tensioning end 204. The second flexible connector 210 has a sliding loop 216, a fixed end 212, and a tensioning end 214. The third flexible connector 220 has a sliding loop 226, a fixed end 222, and a tensioning end 224. The fourth flexible connector 230 has a sliding loop 236, a fixed end 232 and a tensioning and 234.

Figure 21:
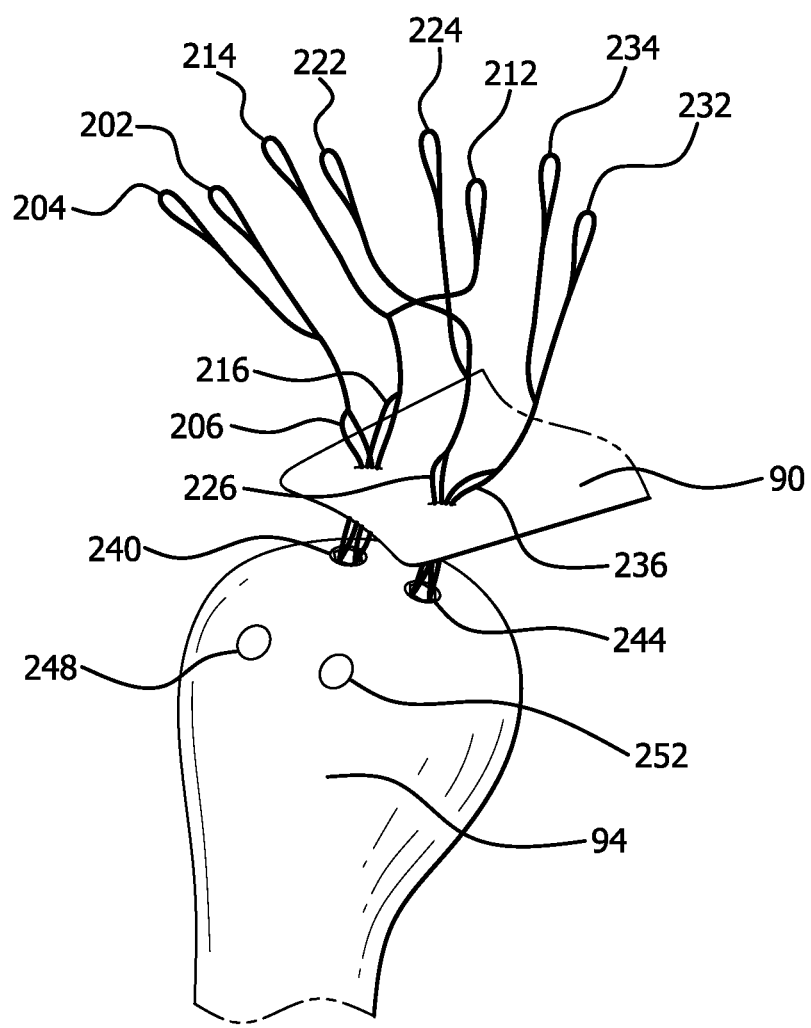
FIG. 21 is a schematic drawing of the orthopedic attachment system of FIG. 19, in a third stage of the orthopedic attachment procedure.

The sliding loop 206 and the sliding loop 216 are attached to a first sliding loop proximal or medial bone anchor 256. The sliding loop 226 and the sliding loop 236 are attached to a second sliding loop proximal or medial bone anchor 260. A first proximal or medial pilot hole 240 and a second proximal or medial pilot hole 244 are formed in the humerus 94. A first distal or lateral pilot hole 248 and a second distal or lateral pilot hole 252 are also formed in the humerus 94. The first sliding loop bone anchor 256 is inserted into the first proximal pilot hole 240. The second sliding loop bone anchor 260 is inserted into the second proximal pilot hole 244, as shown in FIG. 20. The first flexible connector 200, second flexible connector 210, third flexible connector 220, and fourth flexible connector 230 are then passed through the graft 90 as shown in FIG. 21. The graft is placed into position.

Figure 23:
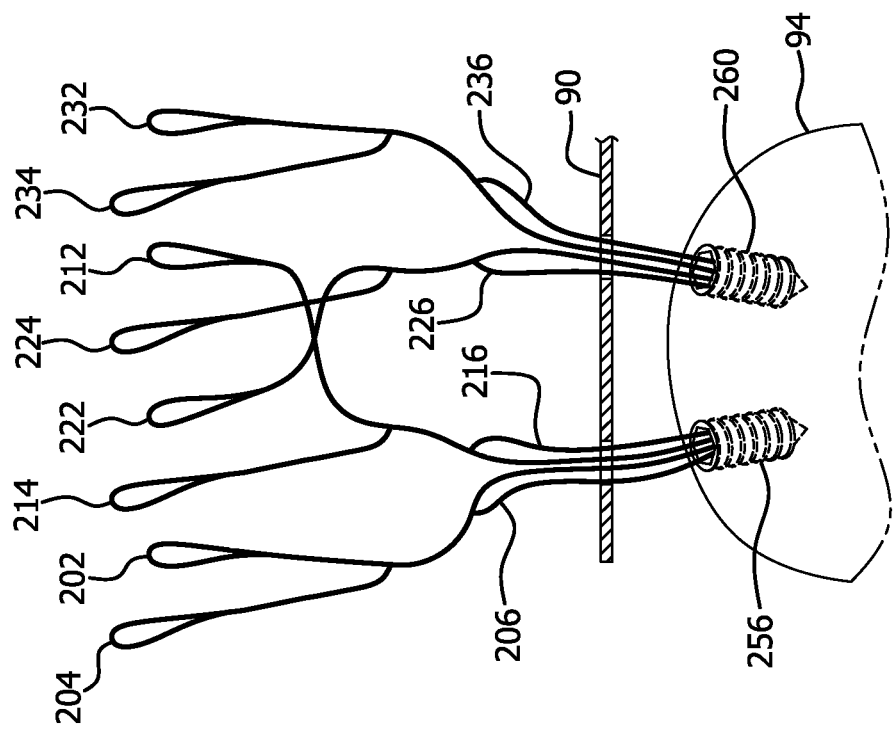
FIG. 23 is a schematic drawing of the orthopedic attachment system of FIG. 19, in a fifth stage of the orthopedic attachment procedure.
Figure 22:
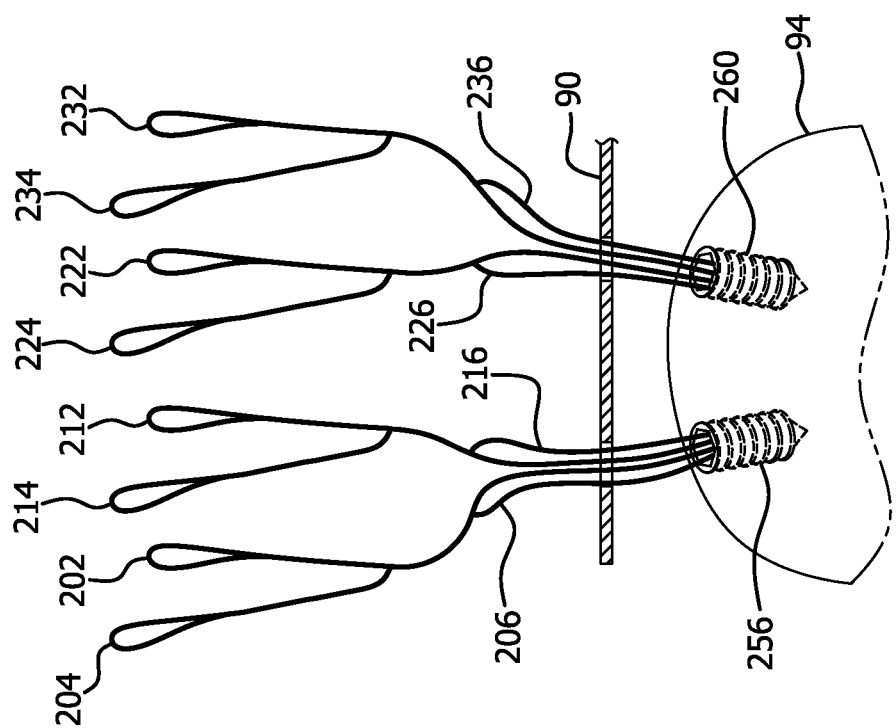
FIG. 22 is a schematic drawing of the orthopedic attachment system of FIG. 19, in a fourth stage of the orthopedic attachment procedure.
Figure 24:
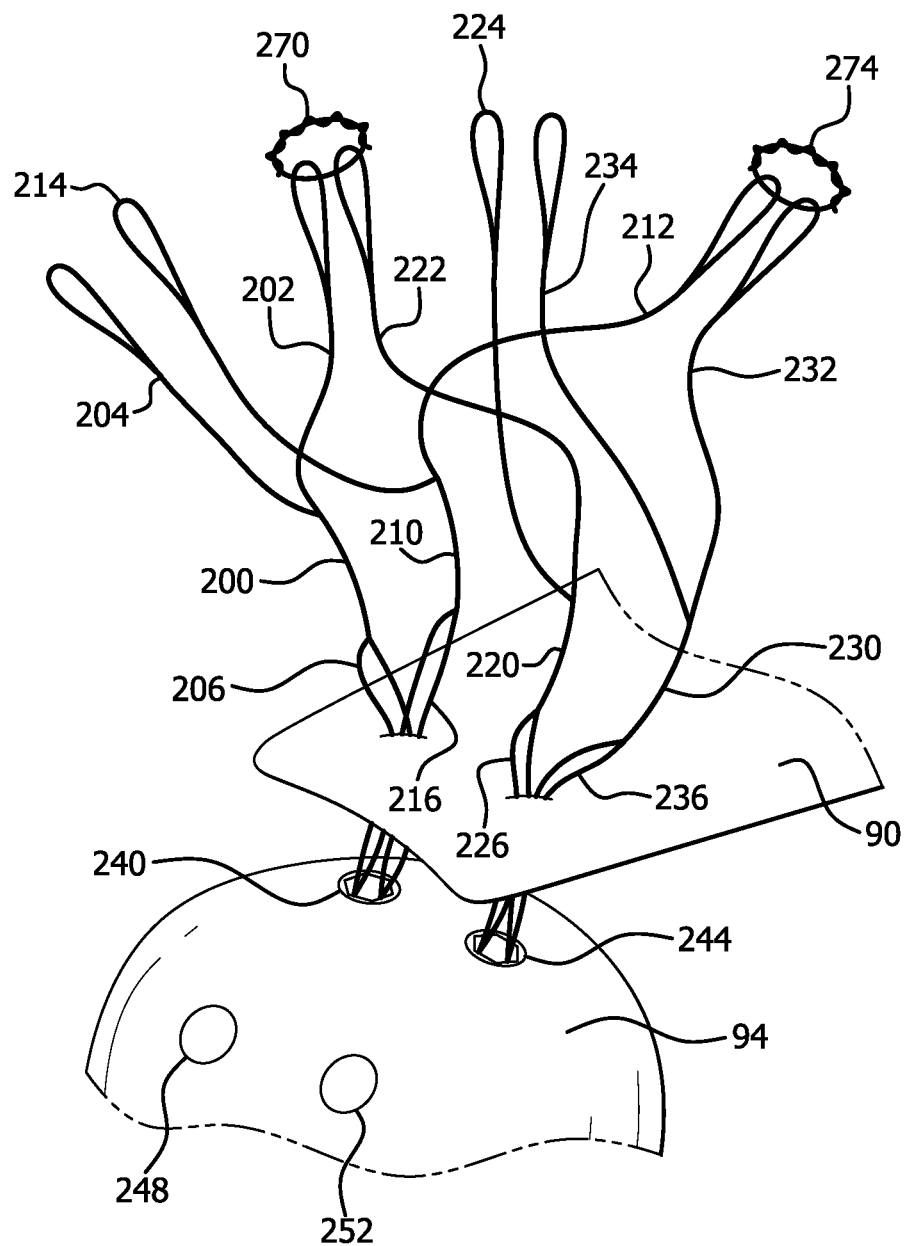
FIG. 24 is a schematic drawing of the orthopedic attachment system of FIG. 19, in a sixth stage of the orthopedic attachment procedure.

The fixed ends of the flexible connectors can be crossed to form an interlaced pattern for securing the graft. This is shown in FIGS. 22-24. After passing through the graft 90, a fixed end that is secured to the first sliding loop bone anchor 256 is attached to one of the fixed ends attached to the second sliding loop bone anchor 260. As shown in FIG. 23, the fixed end 212 of the second flexible connector 210 and the fixed end 222 of the third flexible connector 220 are crossed. As shown in FIG. 24, the fixed end 202 of the first flexible connector 200 and the fixed end 222 of the third flexible connector 220 are connected to a common first fixed end bone anchor 270 such as the all suture anchor shown. The fixed end 214 of the second flexible connector 210 and the fixed end 232 of the fourth flexible connector 230 are connected to a common second fixed end bone anchor 274.

Figure 25:
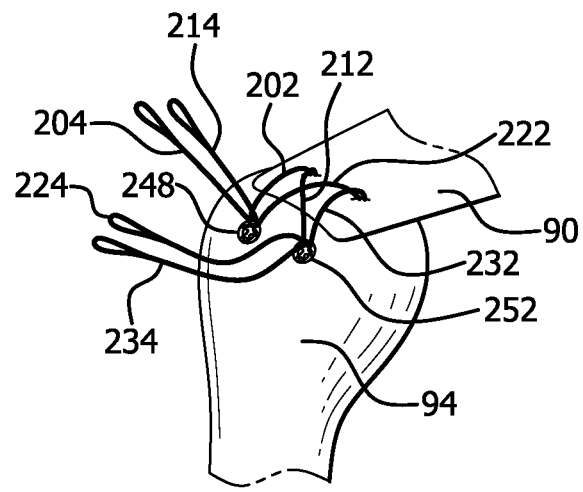
FIG. 25 is a schematic drawing of the orthopedic attachment system of FIG. 19, in the seventh stage of the orthopedic attachment procedure.
Figure 26:
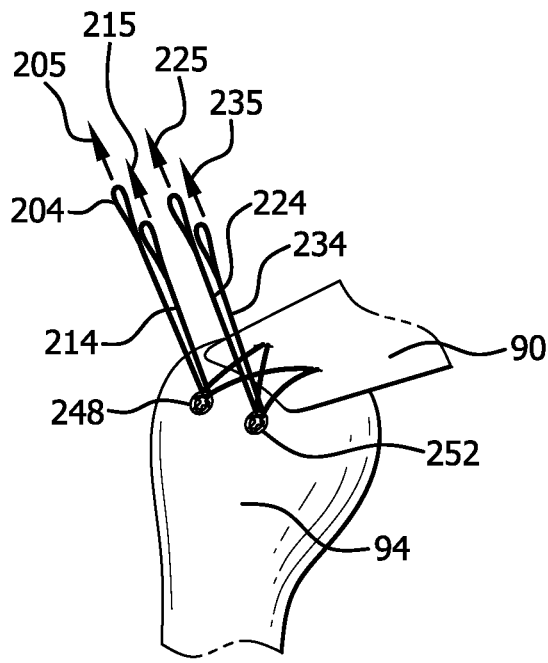
FIG. 26 is a schematic drawing of the orthopedic attachment system of FIG. 19, in an eighth stage of the orthopedic attachment procedure.
Figure 27:
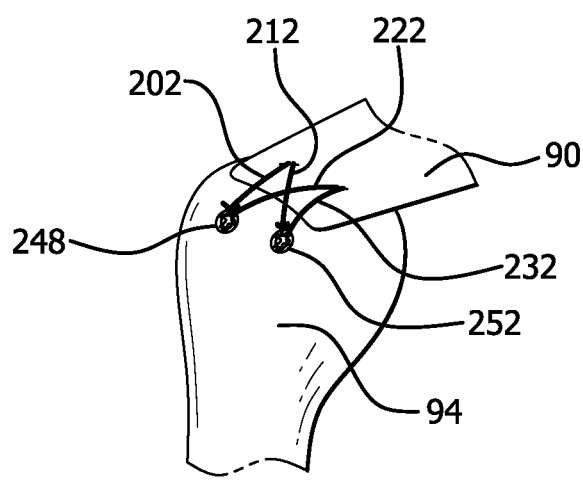
FIG. 27 is a schematic drawing of the orthopedic attachment system of FIG. 19, in a ninth stage of the orthopedic attachment procedure.

The first fixed end bone anchor 270 is then placed in the first distal pilot hole 248. The second fixed end bone anchor 274 is placed in the second distal pilot hole 252. This is shown in FIG. 25. As shown in FIG. 26, tensile forces indicated by arrows 205, 215, 225 and 235 can be applied to tensioning ends 204, 214, 224 and 234, respectively. This will adjust the respective sliding loops and secure the respective tensioning ends to the fixed ends. The graft 90 will be secured to the humerus 94. The tensioning ends 204, 214, 224 and 234 can then be trimmed, as shown in FIG. 27.

Figure 28:
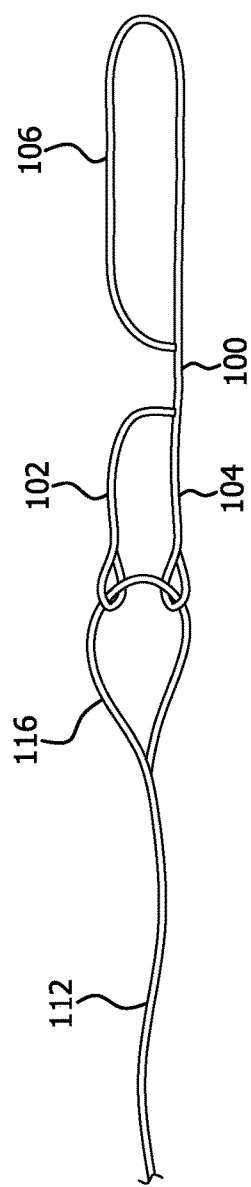
FIG. 28 is a side elevation of a flexible connector with a passing suture.

The flexible connector of the invention can be provided in various assembled forms. There is shown in FIG. 28 an embodiment in which the flexible connector 100 has fixed end 104 and tensioning end 102 secured to loop 116 of suture passer 112. It is also possible to provide the flexible connector with the sliding loop pre-connected to the sliding loop anchor, the fixed end pre-connected to the fixed end anchor, or both.

Figure 33:
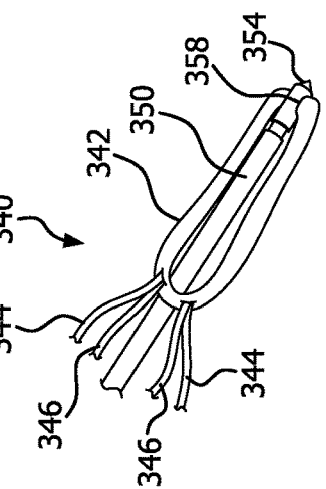
FIG. 33 is a perspective view of a sleeved anchor.
Figure 32:
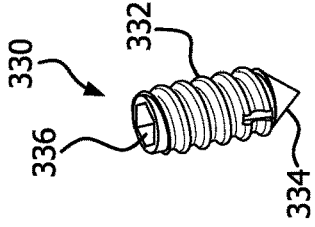
FIG. 32 is a perspective view of a sliding suture anchor.
Figure 31:
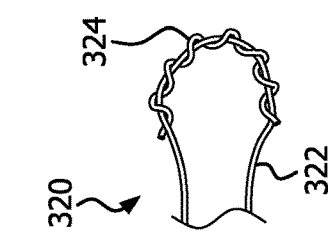
FIG. 31 is a perspective view of an all suture anchor.
Figure 30:
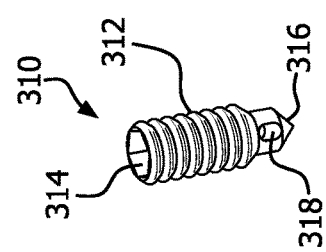
FIG. 30 is a perspective view of a knotless anchor.
Figure 29:
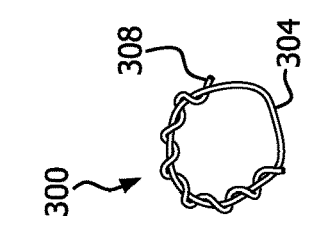
FIG. 29 is a side elevation of an all suture anchor.

The invention can be utilized with a number of different types of bone anchors. FIG. 29 is a side elevation of an all suture anchor 300 having a suture loop 304 and wrapped suture 308. FIG. 30 is a perspective view of a knotless anchor 310 having threads 312, an open interior 314, an aperture 318 and a pointed end 316. FIG. 31 is a perspective view of an all suture anchor 320 having ends 322 and wrapped suture 324. FIG. 32 is a perspective view of a sliding suture anchor 330 having threads 332, a pointed end 334, and open interior 336. FIG. 33 is a perspective view of a sleeved anchor 340 having a sleeve 342 and sutures 344 and 346 which can be used to draw up the sleeve 342 into a wadded ball and secure it in position in the pilot hole. A placement device 350 with tip 354 can be used to place the distal portion 358 of the anchor 340 into position.

Different constructs of the flexible connectors of the invention are possible. There is shown in FIGS. 34-35 a double-sided construct having a first flexible connector 410 with a sliding loop 416 and a tensioning end 414, and a second flexible connector 420 having a sliding loop 426 and a tensioning end 424. A fixed end 412 of the flexible connector 410 and a fixed end 422 of the flexible connector 420 are formed from a common length of flexible connector that forms a loop 438. As shown in FIG. 35, area C in FIG. 34, the common fixed end has an interlocking construction where portion 430 of fixed end 412 is transversely and slidably connected to the fixed end 422 as by penetrating the portion 434 of fixed end 422 at a location 444. Similarly portion 434 is transversely and slidably connected to the fixed end 412 as by penetrating portion 430 at a location 442. Sliding loop 416 can be connected to sliding loop anchor 419 by suture loop 417. Sliding loop 426 can be connected to sliding loop anchor 429 by suture loop 427. A fixed end anchor 450 can be secured by means of suture 454 and disc 458. Alternatively the fixed end anchor 450 could be secured directly to the joint fixed end as at loop 438. The sliding loop anchors 419 and 429 are placed into suitable pilot holes, as is fixed end anchor 450. Tension on tensioning end 414 and tensioning end 424 will cause the sliding loop 416 and sliding loop 426 to tighten and secure the flexible connector 410 and the flexible connector 420 in position.

Figure 36:
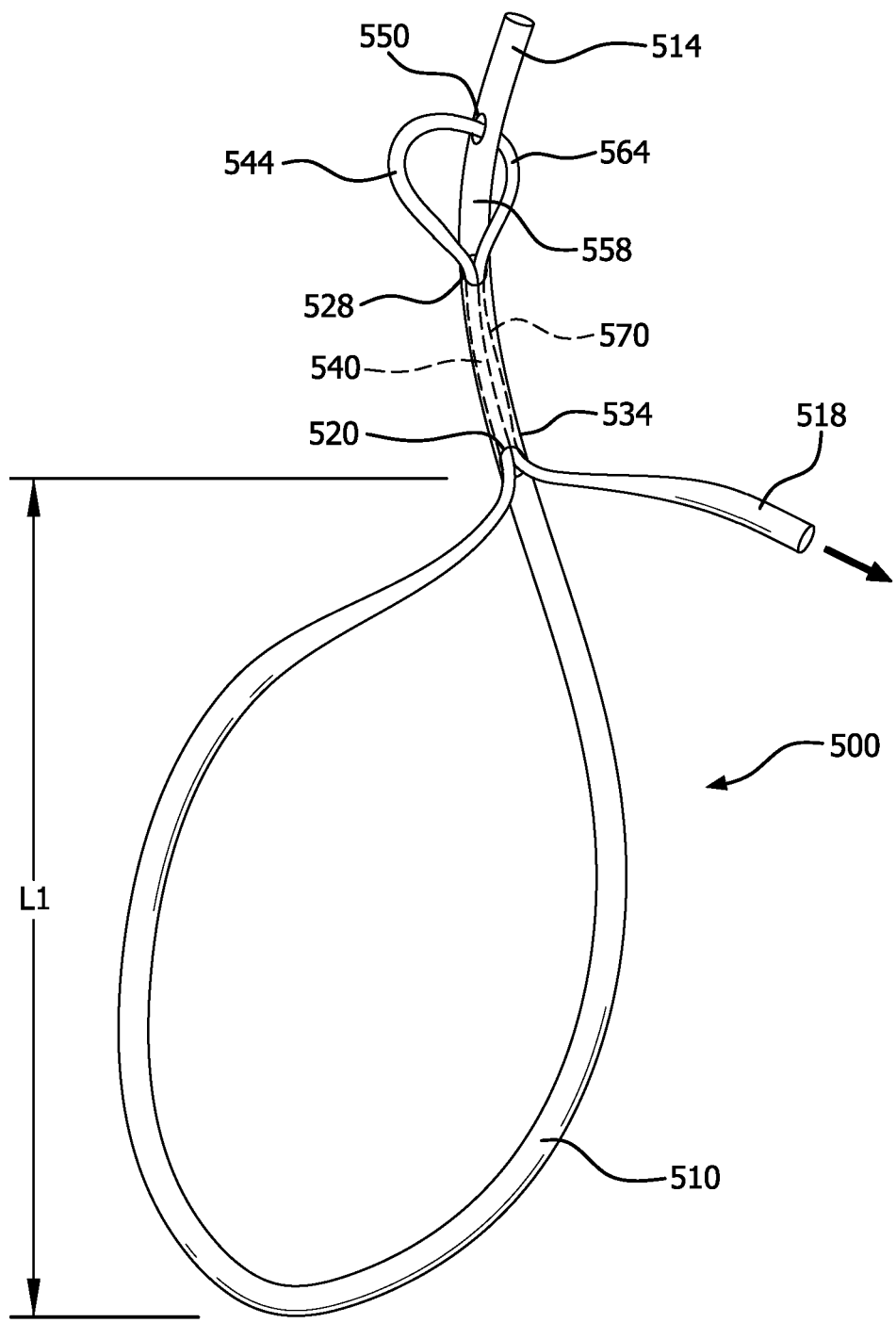
FIG. 36 is a plan view, partially in phantom, of an alternative embodiment of a flexible connector, in a first mode of operation.
Figure 37:
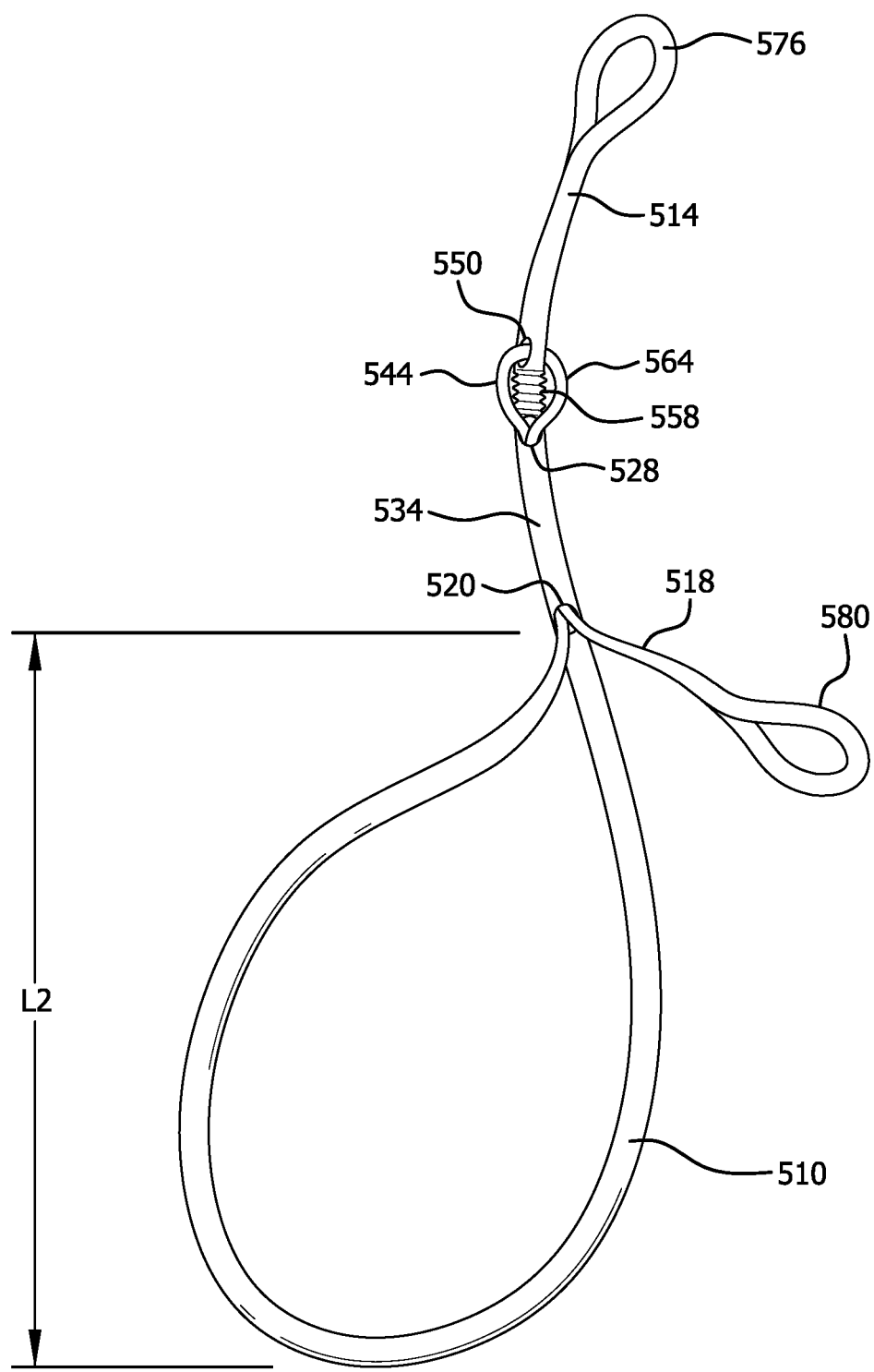
FIG. 37 is a plan view of the embodiment of FIG. 36, partially in phantom, in a second mode of operation.
Figure 38:
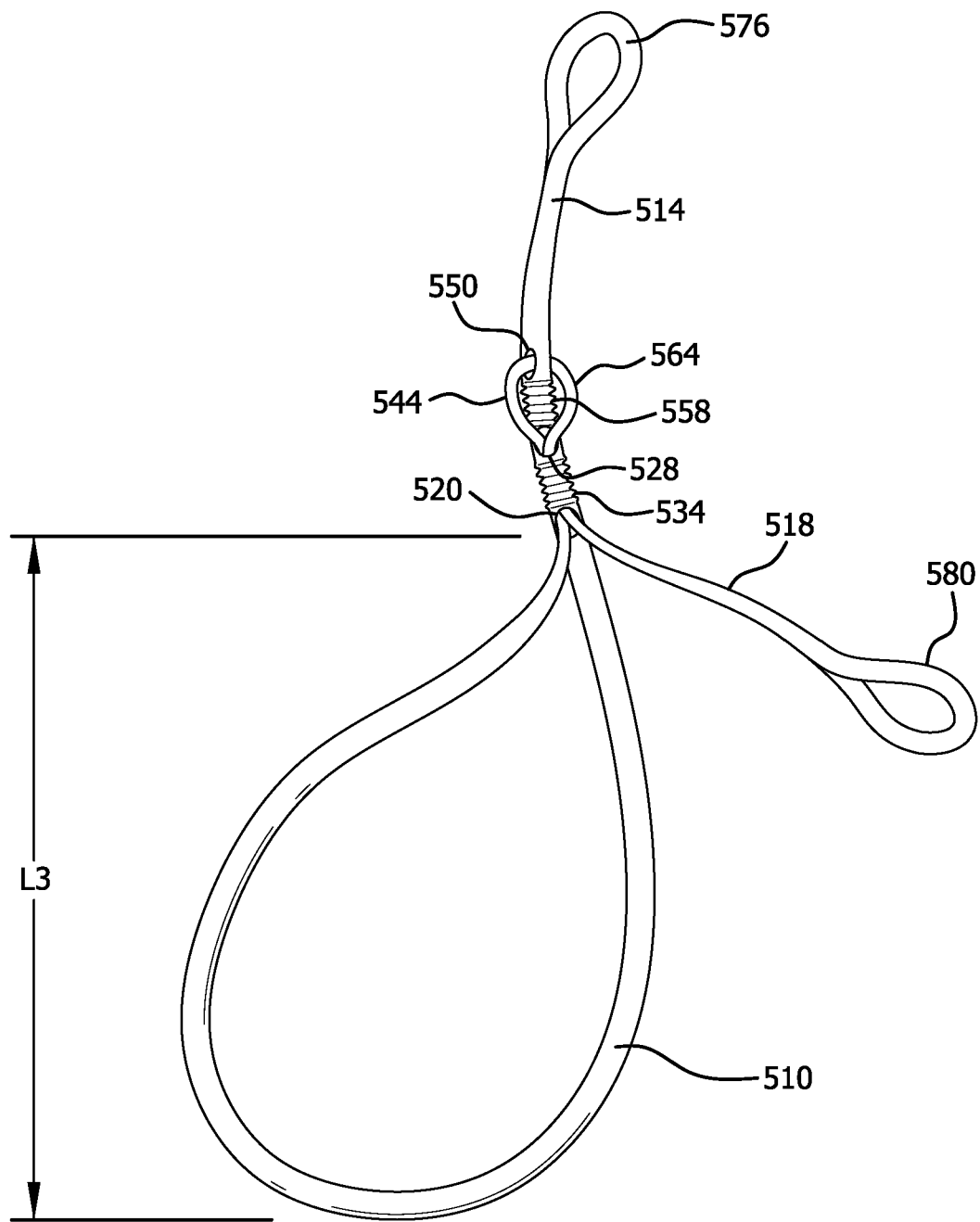
FIG. 38 is a plan view of the embodiment of FIG. 36, partially in phantom, in a third mode of operation.

Another construct of the flexible connector is shown in FIGS. 36-38. The flexible connector 500 includes a fixed end 514 and the tensioning end 518. The tensioning end 518 is threaded through the fixed end 514 to form a sliding loop 510. The tensioning end 518 enters the fixed end 514 at an aperture 520 and portion 540 extends through a portion 534 of the fixed end 514 and exits at an aperture 528. A loop portion 544 is formed by transversely threading the tensioning end 518 through the fixed end 514 at an aperture 550. A second loop portion 564 is formed by causing the tensioning end to re-enter the aperture 528. The portion 570 of the tensioning end 518 traverses the portion 534 of the fixed end 514 and exits at the aperture 520. The forms a second axial sliding connection and serves as a sliding locking connection for lock the tensioning end to the fixed end. In the initial condition the sliding loop 510 has a length L1.

The flexible connector 500 is tightened by applying tension to the tensioning end 518 when the fixed end 514 and the flexible loop 510 are secured in position. A loop 576 can be provided on the fixed end 514 and a loop 580 can be formed in the tensioning end 518 to facilitate attachment and manipulation. As tension is applied to the tensioning end 518, the portion 570 will slide axially in the proximal direction from the aperture 528 toward the aperture 520. The portion 540 will also move axially in the distal direction through the fixed end 514 from the aperture 520 toward the aperture 528. This will cause the loop portions 544 and 564 two exert a force on the portion 558 between the aperture 528 and the aperture 550. The portion 558 will be compressed as shown in FIG. 37. Also, the axial sliding of the portion 540 will cause a reduction in the size of the sliding loop 510 from L1 to L2.

Upon the application of further tension to the tensioning end 518 a compressive force will be applied by the loop portions 544 and 564 between the aperture 520 and the aperture 528. A resulting compressive force will cause compression of the portion 534 as shown in FIG. 38. The portion 540 will continue to move axially between the aperture 520 and the aperture 528. This will result in a further reduction in the dimension of the sliding loop 510 from L2 to L3. The will also serve to lock the tensioning end 518 to the fixed end 514.

It will be apparent from the above that different conformations of the flexible connector are possible. This invention can be embodied in other forms without departing from the spirit or essential attributes thereof. Reference should be made to the appended claims to determine the scope of the invention.

We claim:

1. An orthopedic attachment system having a proximal end and a distal end, the system comprising;
    a flexible connector comprising an elongate member having a fixed end at the distal end of the orthopedic attachment system and a tensioning end, wherein the tensioning end passes through the fixed end forming three connections to the fixed end;
    a first connection of the three connections comprising a sliding axial connection, a sliding loop at the proximal end of the orthopedic attachment system formed by the sliding axial connection of the tensioning end through the fixed end, the tensioning end entering at a proximal entering location on the fixed end and exiting at a distal exiting location on the fixed end,
    a second connection of the three connections comprising a distal transverse sliding connection at the distal end of the orthopedic attachment system, the distal transverse sliding connection formed by the tensioning end passing transversely through the fixed end in a first direction,
    a third connection of the three connections comprising a locking sliding connection at a location along the flexible connector between the distal transverse sliding connection and the sliding axial connection, the locking sliding connection formed by the tensioning end passing transversely through the fixed end in a second direction counter to the first direction;
    wherein the orthopedic attachment system further comprises a sliding loop bone anchor connected to the sliding loop, a fixed end anchor connected to the fixed end, and the tensioning end being slidably connected and lockable to the fixed end;
    wherein upon tension being applied to the tensioning end, a portion of the fixed end between the distal transverse sliding connection and the locking sliding connection is configured to be drawn toward the distal exiting location of the sliding axial connection to form a knot and to secure the orthopedic attachment system in position.

2. The orthopedic attachment system of claim 1, wherein the fixed end of the flexible connector has lateral sides, and the distal transverse sliding connection has an entry and an exit on the fixed end, and the locking sliding connection has an entry and an exit on the fixed end, and wherein the distal exiting location of the sliding axial connection, the entry of the distal transverse sliding connection, and the exit of the locking sliding connection are on the same lateral side of the fixed end of the flexible connector.

3. The orthopedic adjustment system of claim 1, wherein the fixed end and tensioning end of the flexible connector comprise loops.

4. The orthopedic adjust system of claim 1, wherein the fixed end anchor is at least one selected from the group consisting of a knotless anchor, an all suture anchor, and a sleeved suture anchor.

5. The orthopedic attachment system of claim 1, wherein the flexible connector is braided, and the three sliding connections are formed by threading the tensioning end of the braided flexible connector through the fixed end.

6. A method for attaching a flexible connector between at least two bone anchors in a patient's body, comprising the steps of:
   providing the flexible connector of claim 1;
   providing the sliding loop bone anchor of claim 1, the sliding loop being connectable to the sliding loop bone anchor;
   providing the fixed end bone anchor of claim 1, the fixed end being connectable to the fixed end bone anchor;
   connecting the sliding loop of the flexible connector to the sliding loop bone anchor to form a flexible connector assembly;
   installing the flexible connector assembly at a patient target location;
   attaching the fixed end of the flexible connector to the fixed end bone anchor;
   installing the fixed end bone anchor and the fixed end of the flexible connector at a second patient target location; and,
   applying tension to the tensioning end to tension the flexible connector between the sliding loop bone anchor and the fixed end bone anchor, wherein upon tension applied to the tensioning end a portion of the fixed end between the distal transverse sliding connection and the locking sliding connection is configured to be drawn toward the distal exiting location of the sliding axial connection to form a knot and to secure the flexible connector assembly in position.

7. The method of claim 6, wherein the flexible connector and the sliding loop bone anchor are provided as a pre-connected flexible connector assembly.

8. The method of claim 6, wherein the flexible connector, the sliding loop bone anchor, and the fixed end bone anchor are provided as a pre-connected flexible connector assembly.

9. The method of claim 6, wherein a graft is secured to and between the sliding loop and the sliding loop bone anchor, and the fixed end and the fixed end bone anchor.

10. A flexible surgical connector, comprising:
    an elongate member having a distal end and a proximal end, a fixed end at a distal end and a tensioning end, wherein the tensioning end passes through the fixed end forming three connections to the fixed end;
    a first connection of the three connections comprising a sliding axial connection, a sliding loop at the proximal end of the elongate member formed by the sliding axial connection of the tensioning end through the fixed end, the tensioning end entering at a proximal entering location on the fixed end and exiting at a distal exiting location on the fixed end,
    a second connection of the three connections comprising a distal transverse sliding connection at the distal end of the elongate member, the distal transverse sliding connection formed by the tensioning end passing transversely through the fixed end in a first direction,
    a third connection of the three connections comprising a locking sliding connection at a location along the elongate member between the distal transverse sliding connection and the sliding axial connection, the locking sliding connection formed by the tensioning end passing transversely through the fixed end in a second direction counter to the first direction;
    wherein upon tension being applied to the tensioning end, a portion of the fixed end between the distal transverse sliding connection and the locking sliding connection is configured to be drawn toward the distal exiting location of the sliding axial connection to form a knot and to secure the flexible surgical connector in position.

\* \* \* \* \*